(12) United States Patent
Urano et al.

(10) Patent No.: US 8,274,652 B2
(45) Date of Patent: Sep. 25, 2012

(54) DEFECT INSPECTION SYSTEM AND METHOD OF THE SAME

(75) Inventors: Yuta Urano, Yokohama (JP); Kaoru Sakai, Yokohama (JP); Shunji Maeda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 48 days.

(21) Appl. No.: 12/109,363

(22) Filed: Apr. 25, 2008

(65) Prior Publication Data

US 2008/0297783 A1    Dec. 4, 2008

(30) Foreign Application Priority Data

Apr. 25, 2007    (JP) .................................. 2007-115005

(51) Int. Cl.
*G01N 21/00* (2006.01)

(52) U.S. Cl. ............... 356/237.4; 356/237.2; 356/237.5; 356/237.6

(58) Field of Classification Search ..... 356/237.2–237.5
See application file for complete search history.

(56) References Cited

U.S. PATENT DOCUMENTS

| | | | | |
|---|---|---|---|---|
| 5,076,692 | A * | 12/1991 | Neukermans et al. | 356/338 |
| 5,279,703 | A * | 1/1994 | Haberger et al. | 216/94 |
| 5,317,380 | A * | 5/1994 | Allemand | 356/338 |
| 5,822,055 | A | 10/1998 | Tsai et al. | |
| 6,104,481 | A | 8/2000 | Sekine | |
| 6,188,785 | B1 * | 2/2001 | Nakamura et al. | 382/149 |
| 6,366,352 | B1 * | 4/2002 | Goldberg et al. | 356/237.2 |
| 6,833,913 | B1 * | 12/2004 | Wolf et al. | 356/237.2 |
| 7,116,413 | B2 * | 10/2006 | Vaez-Iravani | 356/237.2 |
| 7,123,356 | B1 * | 10/2006 | Stokowski et al. | 356/237.2 |
| 7,379,175 | B1 * | 5/2008 | Stokowski et al. | 356/237.5 |
| 7,388,979 | B2 * | 6/2008 | Sakai et al. | 382/149 |
| 7,456,963 | B2 * | 11/2008 | Shishido et al. | 356/369 |
| 7,672,799 | B2 * | 3/2010 | Shimura et al. | 702/81 |
| 2005/0147287 | A1 * | 7/2005 | Sakai et al. | 382/141 |
| 2005/0253081 | A1 * | 11/2005 | Shishido et al. | 250/372 |
| 2006/0109457 | A1 * | 5/2006 | Miller et al. | 356/237.4 |
| 2007/0008519 | A1 * | 1/2007 | Naftali et al. | 356/237.2 |
| 2007/0052955 | A1 * | 3/2007 | Shishido et al. | 356/237.2 |
| 2007/0206184 | A1 * | 9/2007 | Uto et al. | 356/237.2 |
| 2008/0054166 | A1 * | 3/2008 | Kuzniz et al. | 250/214 VT |
| 2008/0059094 | A1 * | 3/2008 | Shimura et al. | 702/81 |

FOREIGN PATENT DOCUMENTS

JP    62-89336    4/1987

(Continued)

*Primary Examiner* — Tarifur Chowdhury
*Assistant Examiner* — Isiaka Akanbi
(74) *Attorney, Agent, or Firm* — Antonelli, Terry, Stout & Kraus, LLP.

(57) ABSTRACT

In an inspection subject substrate, there is a problem that a defect signal is overlooked due to scattered light from a pattern and sensitivity decreases in an irregular circuit pattern part. The inventors propose a defect inspection method, characterized by comprising: an illumination step of guiding light emitted from a light source to a predetermined area on an inspection subject substrate under a plurality of predetermined optical conditions; a detection step of obtaining an electric signal by guiding scattered light components propagating in a predetermined range of azimuthal angle and in a predetermined range of elevation angle to a detector for each of a plurality of scattered light distributions occurred correspondingly to the plurality of optical conditions in the predetermined area; and a defect determination step of determining a defect based on the plurality of electric signals obtained in the detection step.

16 Claims, 15 Drawing Sheets

FOREIGN PATENT DOCUMENTS

| | | |
|---|---|---|
| JP | 63-135848 | 6/1988 |
| JP | 01-117024 | 5/1989 |
| JP | 01-250847 | 10/1989 |
| JP | 06-258239 | 9/1994 |
| JP | 06-324003 | 11/1994 |
| JP | 08-210989 | 8/1996 |
| JP | 2007-327815 | 12/2007 |
| JP | 2008-20374 | 1/2008 |

* cited by examiner (a)

(b)

(a)

(b)

(a)

| | Lengthwise/Sidewise/Diagonal pattern shading | Forward scattering shading | Backward scattering shading |
|---|---|---|---|
| 45°-oriented illumination |  |  |  |
| 90°-oriented illumination |  |  |  |
| Coaxial vertical illumination |  |  |  |

(b)          (c)          (d)

Lengthwise/Sidewise/periodical pattern shading (45°-oriented illumination)

(a)

(b)

(a)

(b)

1) Whole area of die
2) Area successively cut from an image sequentially grabbed
3) Specific area in die
4) Same areas of a plurality of dies

DEFECT INSPECTION SYSTEM AND METHOD OF THE SAME

The present application claims priority from Japanese application serial no. JP 2007-115005, filed on Apr. 25, 2007, the content of which is hereby incorporated by reference into this application.

BACKGROUND OF THE INVENTION

1. Field of the Invention

The present invention relates to a defect inspection system that in a manufacture process for manufacturing an object by forming a pattern on a substrate, such as a semiconductor manufacture process, a liquid crystal display device manufacture process, and a printed circuit board manufacture process, inspects an occurrence status of a defect, such as a foreign substance, in manufacture steps of detecting a defect occurred, such as a foreign substance, analyzing it, and taking action, and a method therefor.

2. Description of the Related Art

In the conventional semiconductor manufacture process, if a foreign substance exists on a semiconductor substrate (an inspection subject substrate to be examined) it will become a failure cause of bad insulation of wiring, short circuit, etc. Further, if a semiconductor device becomes a very small and a minute foreign substance exists in the semiconductor substrate, this foreign substance might become a cause of bad insulation of a capacitor and breakage of a gate oxide film etc. Various causes give rise to these foreign substances and make them exist on the substrate in various states, such as occurring from a movable part of a conveyance apparatus, occurring from a human body, occurring by a reaction of a process gas in a processing system, or being mixed in chemicals and materials.

In a similar manufacture process of a liquid crystal display device, if any defect occurs, such as intermixing of a foreign substance on the pattern, the liquid crystal display device becomes unusable as a display device. A situation is the same also in the manufacture process of a printed circuit board; intermixing of a foreign substance becomes a cause of short circuit or poor connection of the pattern.

As one of conventional technologies of this kind of detecting the foreign substance on a substrate, there is a technology, as described in JP-A No. S62 (1987)-89336 (Patent document 1), that makes it possible to perform high-sensitivity and high-reliability foreign substance and defect inspection while eliminating a false report due to the pattern by detecting scattered light from a foreign substance that is occurred when the foreign substance adheres to a semiconductor substrate, by irradiating laser light onto the semiconductor substrate and by comparing it with an inspection result of a semiconductor substrate of the identical kind that was inspected just before this detection. Moreover, as disclosed by JP-A No. S63 (1988)-135848 (Patent document 2), there is a technique that detects scattered light from the foreign substance occurred in the case where the foreign substance adheres onto the semiconductor substrate by irradiating laser light on the semiconductor substrate, and analyzes the foreign substance so detected with a analysis technology, such as laser photoluminescence or secondary X-ray analysis (XMR).

Moreover, as a technique of inspecting the foreign substance, there is known a method where the inspection subject substrate is illuminated with coherent light, light emitted from a repeating pattern on the inspection subject substrate is removed by a spatial filter, and a foreign substance and a defect having no repeatability are emphasized and detected.

Moreover, JP-A No. H1 (1989)-117024 made a foreign substance inspection system to be known that irradiates illumination light to a circuit pattern formed on the inspection subject substrate from a direction inclined by 45° with respect to a main straight line group of the circuit pattern and prevents the zeroth order diffracted light from the main straight line group from entering into an aperture of the objective lens. In this conventional technology 3, the document also describes that other straight lines that are not main straight line group are shaded by a spatial filter.

In addition, as conventional technologies about defect inspection systems for foreign substances and the methods therefor, the following Patent documents are known: JP-A No. H1 (1989)-250847 (Patent document 4), JP-A No. H6 (1994)-258239 (Patent document 5), JP-A No. H6 (1994)-324003 (Patent document 6), JP-A No. H8 (1996)-210989 (Patent document 7), and JP-A No. H8 (1996)-271437 (Patent document 8).

Furthermore, U.S. Pat. No. 5,822,055 (Patent document 9) made a defect inspection system and a method therefor to be known that detects a defect using a luminance difference between dies that are inspection results, respectively, by simultaneously performing the bright visual field illumination and the dark visual field illumination.

However, the conventional technologies of the Patent documents 1 to 8 have a problem that in an irregular circuit pattern part, a defect signal may be overlooked due to the scattered light from the pattern, which results in decreased sensitivity.

Although in the Patent document 9, high-accuracy alignment is realized by using a bright visual field image, in order to obtain contrast of the defect part in the bright visual field image, an image must be obtained in a small image size that is comparable to the defect size or a few times larger than it or less by increasing a magnification. For this reason, there is a problem that inspection area per unit time is small which decreases throughput. Moreover, since the bright visual field illumination and the dark visual field illumination illuminate the identical place simultaneously, a scattered light distribution occurred thereby is unique. Therefore, there is a problem that the scattered light distribution occurred by the bright visual field illumination and the scattered light distribution occurred by the dark visual field illumination cannot detect respective features individually. Furthermore, since only the luminance difference between dies in each detection result is used, there is a problem that optical characteristics other than it (polarization, phase, etc.) or features on the image (contrast etc.) cannot be detected.

SUMMARY OF THE INVENTION

To address the problem, the present invention aims at providing a defect inspection system configured to be capable of inspecting a defect on an inspection subject substrate that has a pattern generating scattered light whose intensity is comparable to that of a defect at high speed and with high accuracy, and a method therefor.

In order to attain the object, the present invention is characterized by having: an illumination step of guiding light emitted from a light source to a predetermined area on the inspection subject substrate under a plurality of predetermined optical conditions; a detection step of obtaining an electric signal by guiding a scattered light component propagating in a predetermined range of azimuthal angle and in a predetermined range of elevation angle for each of the plurality of scattered light distributions occurred correspondingly to the plurality of optical conditions in the predetermined area; and a defect determination step of determining a defect based on a plurality of electric signals obtained in the detection step.

Moreover, the present invention is characterized by having: an illumination step of guiding light emitted from a light source to a predetermined area on the inspection subject substrate under a plurality of predetermined optical conditions; a detection step of obtaining a plurality of electric signals by guiding the scattered light component including in a predetermined range of a plurality of optical conditions for each of the plurality of scattered light distributions occurred correspondingly to the plurality of optical conditions in the predetermined area; and a defect determination step of determining a defect based on the plurality of electric signals obtained in the detection step.

The present invention is characterized by having: an illumination step of guiding light emitted from a light source to a predetermined area on the inspection subject substrate under a predetermined optical condition; a detection step of obtaining a plurality of electric signals by guiding the scattered light distribution included in a predetermined range of a plurality of optical conditions regarding the scattered light distribution occurred in the predetermined area; and a defect determination step of determining a defect based on the plurality of electric signals obtained in the detection step.

The present invention is characterized in that in the detection step, only light components of the light components occurred in the illumination step from which specularly reflected light components are eliminated are detected.

According to the present invention, a very small defect can be inspected at high speed and with high accuracy for the inspection subject substrate in which a pattern generating the scattered light exists.

BRIEF DESCRIPTION OF THE DRAWINGS

FIGS. 3A and 3B are configuration diagrams of an illumination unit in the defect inspection system related to the present invention, in which FIG. 3A shows the configuration of the illumination unit, and FIG. 3B shows a configuration up to the inspection subject substrate after the reflection.

FIGS. 4A and 4B are configuration diagrams of a detection unit in the defect inspection system related to the present invention, in which FIG. 4A shows the detection unit and FIG. 4B shows an optical system for observing a light intensity distribution on an exit pupil plane.

FIGS. 5A, 5B, 5C, and 5D are explanatory diagram of a filter unit in the defect inspection system related to the present invention, in which FIG. 5A shows examples of shapes of shading parts and transmission parts of spatial filters, FIG. 5B shows another example of the spatial filter, FIG. 5C shows a two-dimensional array of shading filter, and FIG. 5D shows a one-dimensional array of shading filter.

FIGS. 6A, 6B, and 6C are relative relations between the illumination unit and the detection unit in the defect inspection system related to the present invention, in which FIG. 6A shows a configuration that specularly reflected light does not enter an objective lens, FIG. 6B shows a configuration with an additional objective lens disposed slantingly, and FIG. 6C shows a configuration of coaxial vertical illumination.

FIG. 7 is a configuration diagram showing a modification example of the illumination unit in the defect inspection system related to the present invention, in which FIG. 7A shows illumination where fields of illumination do not overlap mutually, and FIG. 7B shows an imaging optics of FIG. 7A.

FIGS. 9A and 9B are configuration diagrams showing a modification example of the detector in the defect inspection system related to the present invention, in which FIG. 9A shows a configuration that separates scattered light according to polarization condition, and FIG. 9B shows the detector for obtaining a plurality of detection signals derived from mutually different polarization components.

FIGS. 11A and 11B are explanatory diagrams showing a detection method in a modification example of the defect inspection system related to the present invention, in which FIG. 11A shows a method for changing an illumination condition, and FIG. 11B a pulsed illumination output, an illumination condition, a detection condition, a temporal relation of ON/OFF of exposure of the detector with a horizontal axis representing time.

FIGS. 13A and 13B are configuration diagrams showing a preprocessing unit in the defect inspection method related to the present invention, in which FIG. 13A shows a configuration of the preprocessing unit, and FIG. 13B shows another configuration example of the preprocessing unit.

FIGS. 14A and 14B are configuration diagrams showing a determination unit in the defect inspection method related to the present invention, in which FIG. 14A shows a configuration of the determination unit, and FIG. 14B.

FIGS. 15A to 15F are explanatory diagrams of the defect determination processing method in the defect inspection method related to the present invention; in which FIG. 15A shows a defect determination method in a case where features are two, FIG. 15B shows a case where a larger number of features are used, FIG. 15C shows selection of a feature or a combination of features that is effective, FIG. 15D shows a case where a combination of features or the features given weights that are different from FIG. 15C are plotted, FIG. 15E shows plotting of the amount of change of the feature between FIG. 15C and FIG. 15D, and FIG. 15F shows pseudo-defect determination processing in pseudo-defect removal processing unit.

DETAILED DESCRIPTION OF THE PREFERRED EMBODIMENTS

Embodiments of the present invention will be described using FIG. 1 to FIG. 20. Below, explanations will be given taking as an example defect inspection on a semiconductor wafer.

Figure 1:
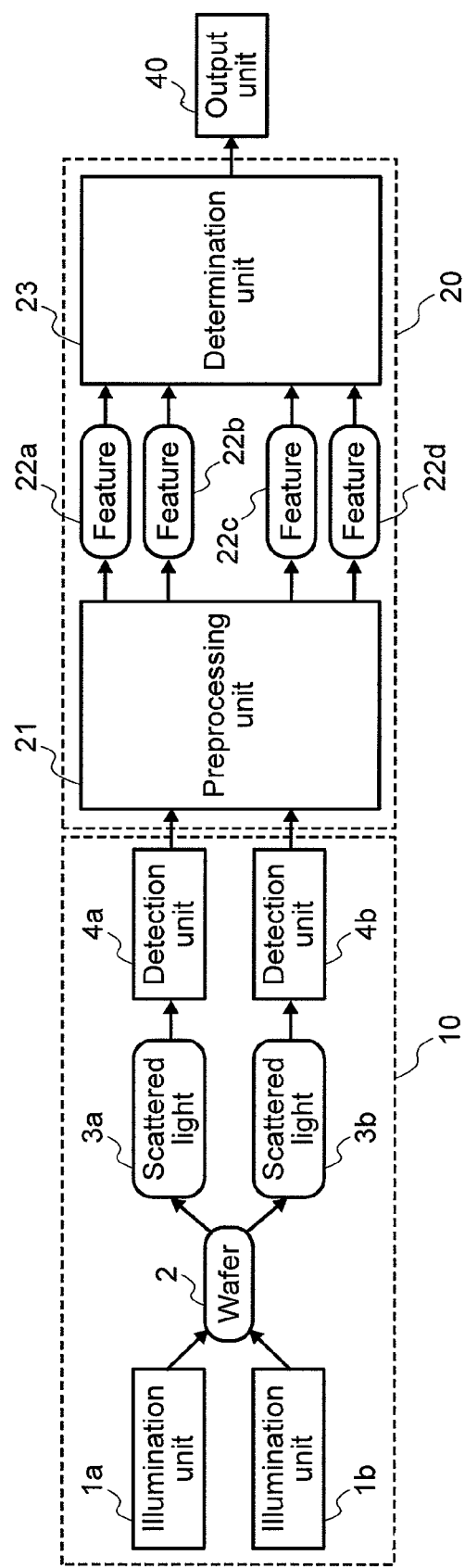
FIG. 1 is a block diagram showing a defect inspection method related to the present invention.

FIG. 1 shows a configuration of the present invention. An optical unit 10 is constructed with a plurality of illumination units 1a, 1b and a plurality of detection units 4a, 4b. The illumination units 1a, 1b irradiate mutually different illumination light to an inspection subject substrate 2. Illumination light coming from the respective illumination units 1a, 1b generate scattered light 3a, 3b, which are detected by the respective detection units 4a, 4b as scattered light intensity signals. The detected scattered light intensity signals are inputted into a processing unit 20. The processing unit 20 is made up of a preprocessing unit 21 and a determination unit 23. The plurality of scattered light intensity signals detected by the optical unit 10 are inputted into the preprocessing unit 21. The preprocessing unit 21 performs the preprocessing that will be described later, such as signal correction, alignment, and feature extraction, on each input signal and outputs one or a plurality of features 22a, 22b, 22c, and 22d for one input signal. The determination unit 23 performs defect determination processing that will be described latter using a plurality of features 22a, 22b, 22c, and 22d inputted from the preprocessing unit 21, and outputs defect information. The output unit 40 outputs the defect information obtained from the processing unit 20 in the form understandable to the user.

The scattered lights 3a, 3b designate distributions of scattered light occurred correspondingly to the illumination units 1a, 1b, respectively. If an optical condition of the illumination light by the illumination unit 1a differs from the optical condition of the illumination light by the illumination unit 1b, the scattered light 3a and the scattered light 3b that are occurred thereby, respectively, differ from each other. In this specification, an optical property of the scattered light occurred by certain illumination light and its characteristics are called a scattered light distribution of the scattered light. More specifically, the scattered light distribution refers to a distribution of an optical parameter value, such as intensity, amplitude, phase, polarization, wavelength, coherency, to an exist position, an exit orientation, and an exit angle of the scattered light.

Figure 2:
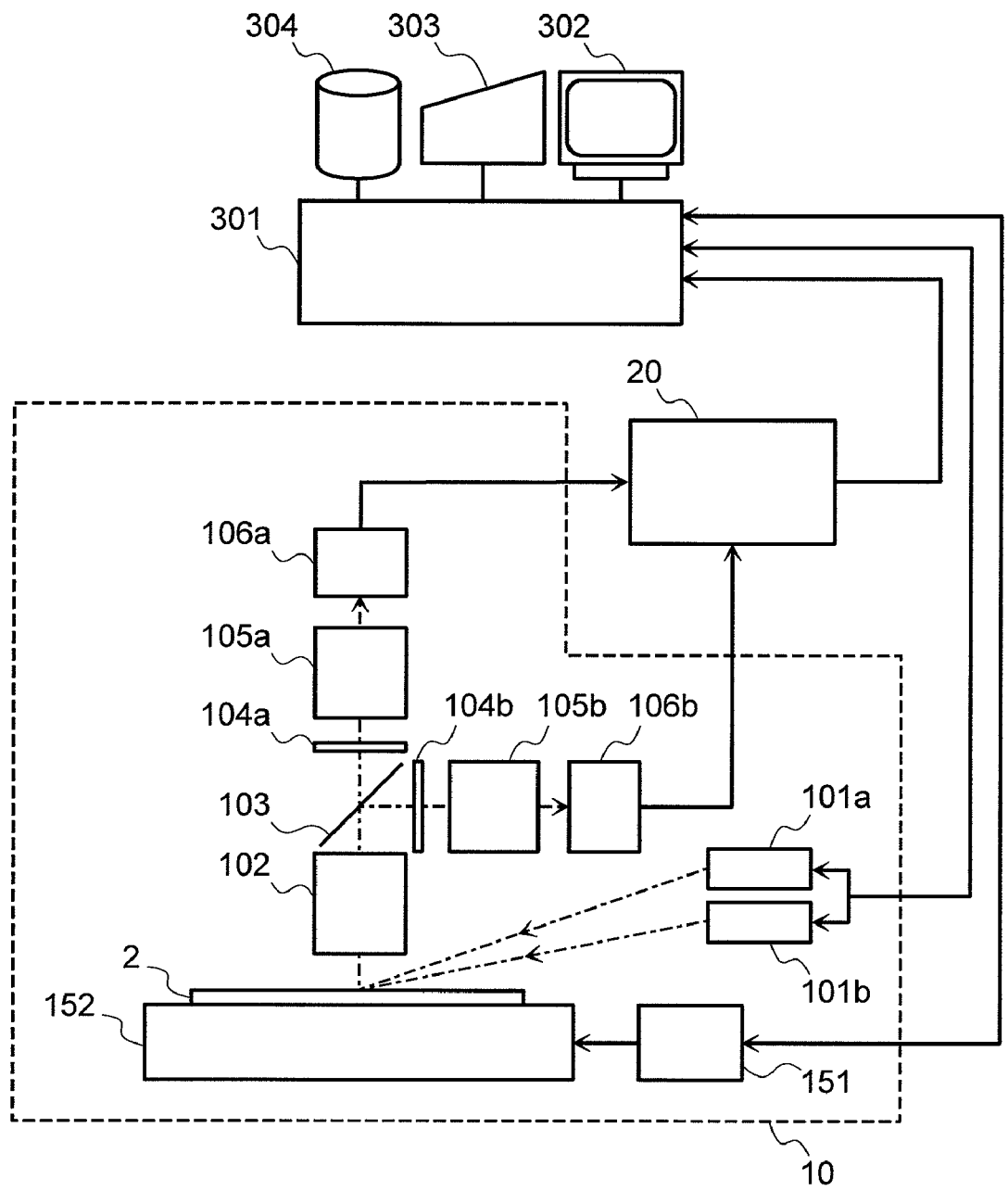
FIG. 2 is a configuration diagram showing a configuration of the defect inspection system related to the present invention.
Figure 3:
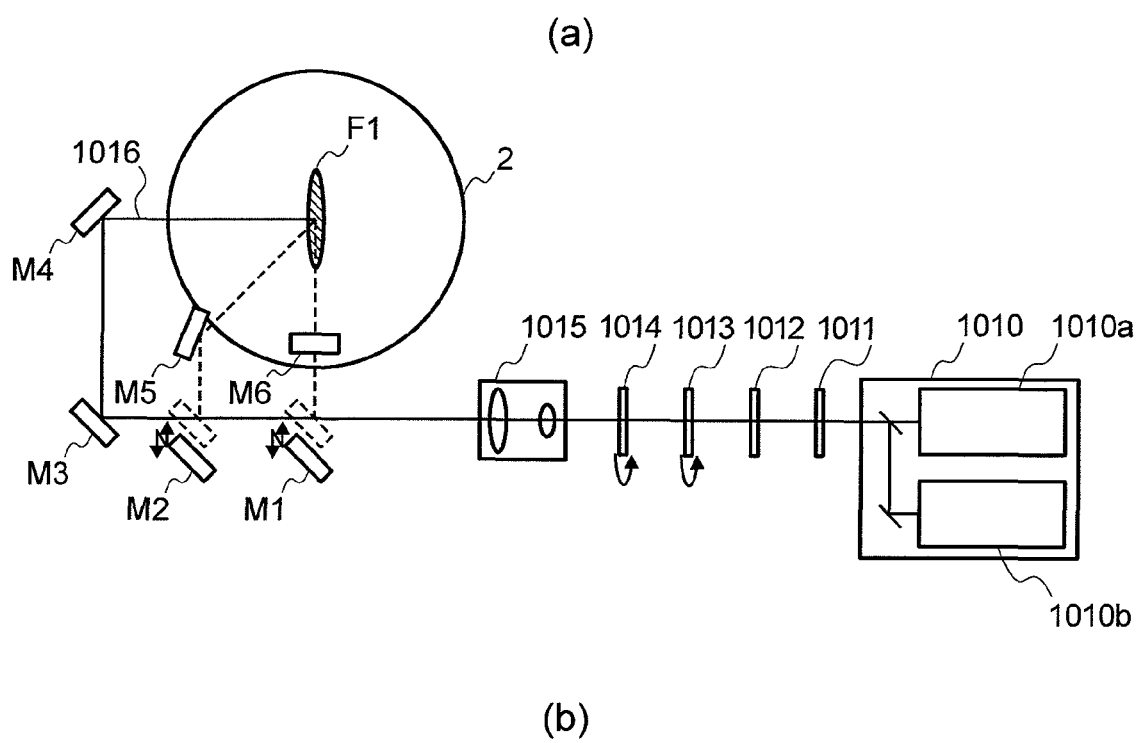
Figure 3:
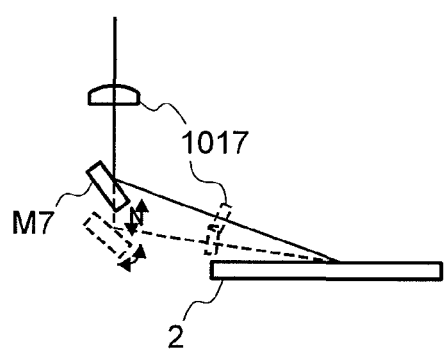

FIG. 2 shows a concrete system configuration to realize a configuration of FIG. 1. The system shown in FIG. 2 is constructed with illumination units 101a, 101b, an objective lens 102, an optical path branching element 103, filter unit 104a, 104b, imaging lenses 105a, 105b, detection units 106a, 106b, the processing unit 20, a total control unit 301, a display unit 302, an operation unit 303, a storage unit 304, a stage drive unit 151, and an X-Y-Z-θ stage 152. The illumination units 101a, 101b, the objective lens 102, an optical path branching element 103, the filter units 104a, 104b, the imaging lenses 105a, 105b, the detection units 106a, 106b, the stage drive unit 151, and the X-Y-Z-θ stage 152 constitute the optical unit 10. Moreover, the system is equipped with a review microscope (not illustrated) capable of obtaining a static image (optical microscope image or electron microscope image) at an arbitrary position on the inspection subject substrate 2.

An outline of operations will be explained. The illumination light is irradiated onto the inspection subject substrate 2 by the illumination units 101a, 101b. The scattered light emitted from the inspection subject substrate 2 is focused by the objective lens 3, and subsequently the optical path branching element 103 branches its optical path into two. A portion of the light propagating on the one path is converted into an electric signal by the detection unit 106a through the spatial filter 104a and the imaging lens 105a. Other portion of the light propagating on the other path is converted into an electric signal by the detection unit 106b through the spatial filter 104b and the imaging lens 105b. Based on the plurality of obtained electric signals, a defect is determined in the processing unit 20. The determined result is stored in the storage unit 304 through the total control unit 301, and is displayed in the display unit 302.

FIG. 3A shows a configuration of the illumination unit. Here, shown is an example of performing illumination of a plurality of mutually different wavelengths. An illumination light source 1010 includes light sources 1010a, 1010b that emit a plurality of mutually different wavelengths, emitting the plurality of lights having mutually different wavelengths almost in the same optical axes. If a single light source emitting lights of a plurality of wavelengths is used as the illumination light source 1010, alignment to make the optical axes coincide with one another becomes unnecessary. As a light source used for the illumination light source 1010, in order to illuminate the inspection subject substrate 2 with high illuminance, a laser light source is suitable. In order to increase scattering efficiency of minute defects, light sources of a deep ultraviolet light laser, a vacuum ultraviolet light laser, the third or fourth harmonic wave of YAG laser, a mercury lamp, a xenon lamp, etc. that are of short wavelengths are suitable. Moreover, in order to hold down costs of parts constituting the optical unit and maintenance cost, light sources of visible light wavelengths, such as the second harmonic wave of YAG laser, a halogen lamp, a mercury lamp, and a xenon lamp, are suitable.

The illumination light emitted from the light source 1010 is controlled in intensity by an attenuator 1011. A polarizing plate 1012 is installed as necessary, and polarization of the illumination light emitted from the light source is rendered to have linear polarization. Phase plates 1013, 1014 set a polarization state of the illumination light arbitrarily. The phase plates 1013, 1014 is each made up of a λ/2 plate capable of rotating light passing therethrough, or a λ/4 plate, or an optical element capable of controlling an amount of phase of a component vibrating in a specific orientation. A beam diameter of the illumination light is enlarged by a beam expander 1015. The illumination light is guided to a field of illumination F1 on the inspection subject substrate 2 by a group of mirrors M1 to M7 through a beam forming element 1017. Below, a case where an optical path 1016 is taken will be explained as an example. By making the mirrors M1 and M2 retreat from on the optical path, the illumination light is reflected by the mirror M3 and mirror M4 to take the optical path 1016. FIG. 3B is a side view showing a configuration up to the inspection subject substrate 2 after the reflection by the mirror M4. By disposing a cylindrical lens in the optical path properly as the beam forming optical element 1017, the illumination light is focused in the area of field of illumination F1 in the shape of a long and slender ellipse on the inspection subject substrate 2. By forming a field of illumination in the form of a line or in the form of a rectangle or circle having large area, an inspection area per unit time is increased, so that high-speed inspection is realized. Alternatively, high-resolution inspection is conducted by focusing light to a point spot using a lens as the beam forming optical element 1017 and scanning the spot in the area. Alternatively, using a Diffractive Optical Element (DOE) a homogenizer, etc. as the beam forming optical element 1017 forms on the inspection subject 2 the field of illumination F1 of an arbitrary shape and an arbitrary illuminance distribution. Moreover, deposition of the mirror group M1 to M7 and an insertion/retreat mechanism thereof set the incident angle and azimuthal angle of the illumination to the inspection subject substrate 2 in ranges that do not interfere with other parts of the optical unit based on an optical condition setup that will be described later.

Figure 4:
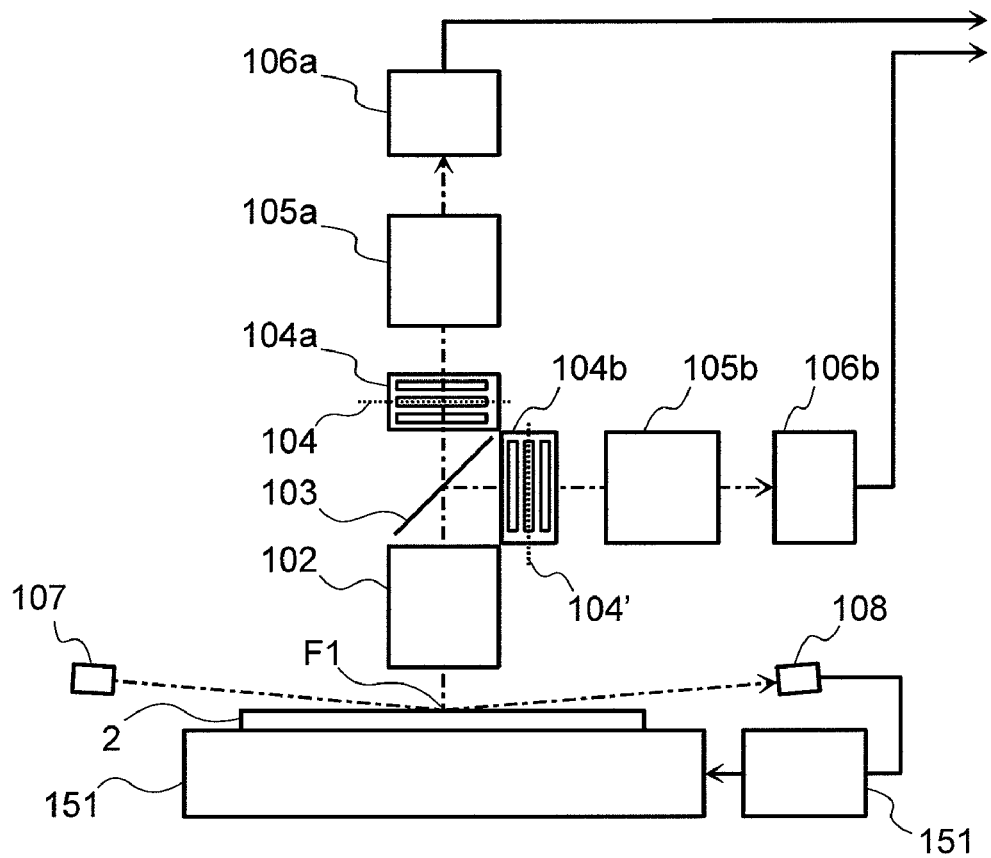
Figure 4:
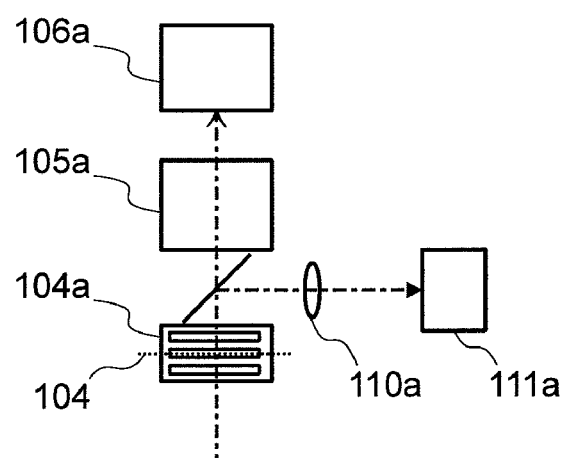
Figure 5:
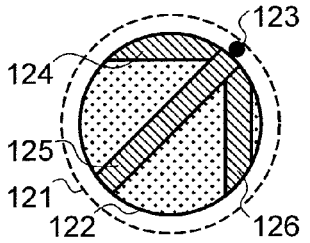
Figure 5:
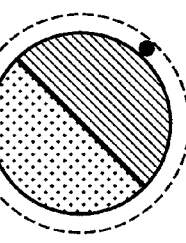
Figure 5:
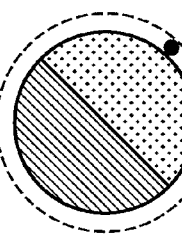
Figure 5:
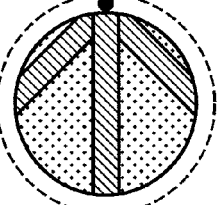
Figure 5:
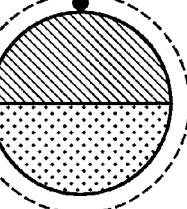
Figure 5:
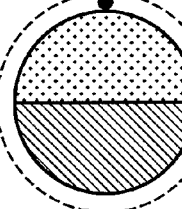
Figure 5:
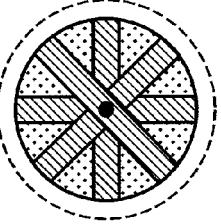
Figure 5:
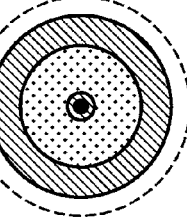
Figure 5:
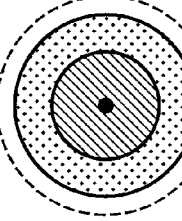
Figure 5:
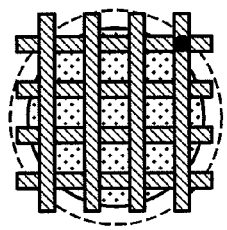
Figure 5:
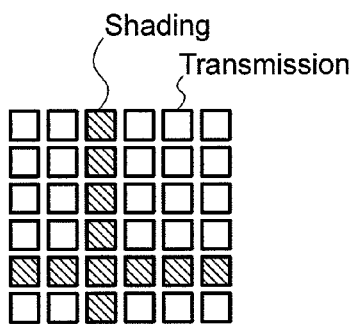
Figure 5:
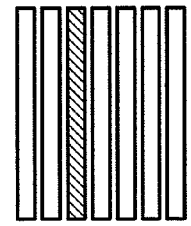

FIG. 4 shows a configuration of the detection unit. The scattered light occurred in the field of illumination F1 on the inspection subject 2 that is irradiated by the illumination unit is focused by the objective lens 102, and is divided by the optical path branching element 103. Subsequently, the divided light is imaged onto each detector 106a (106b) by the imaging lens 105a (105b) An auto focusing illumination unit 107 and an auto-focusing detection unit 108 constitute an auto focusing optical system. By the auto-focusing detection unit 108 measuring a displacement of a projected image by the auto focusing illumination unit 107, a displacement in the height direction of the inspection subject 2 is measured. In order to prevent a fall of defect inspection sensitivity due to defocusing, when the height displacement of the inspection subject 2 exceeds a predetermined permissible value, a control by the stage drive unit 151 is performed to the X-Y-Z-θ stage 152 so that the displacement may be suppressed.

In the case where the plurality of lights having mutually different wavelengths are used, it is desirable that as the objective lens 102, a reflective type objective lens or a reflective refraction type (catadioptric type) objective lens is used in order to suppress color aberration. Moreover, the objective lens 102 forms an exit pupil plane or its conjugate plane 104 on the opposite side of the inspection subject 2 across the objective lens 102. Using a Fourier transform lens as the objective lens 102 forms an image of diffracted lights of the orthogonal diffraction grating on the surface of the inspection subject 2 in the form of an orthogonal grating on the exit pupil plane, and spatial filtering that will be described later functions effectively. Moreover, in order to prevent variation of the magnification due to a relative height variation of the inspection subject 2 and the detectors 106a, 106b, a combination of the objective lens 102 and the imaging lens 105a or a combination of the objective lens 102 and the imaging lens 105b constitutes an object-side telecentric optical system or a both-side telecentric optical system.

By using a dichroic mirror to switch the light to a different optical path depending on wavelength as the optical path branching element 103, the scattered light occurred is separated for each illumination wavelength, and each of the detectors 106a, 106b detects the separated light independently. Alternatively, by using a polarizing beam splitter as the optical path branching element 103, an optical path is branched so that each polarization may be given to each optical path and is detected independently. Moreover, if a half mirror is used as the optical path branching element 103, a scattered light component that accords to a filter being set up in each of the filter units 104a, 104b is detected.

The filter units 104a, 104b are installed on the exit pupil planes 104, 104' originated by the objective lens 102, respectively. FIG. 5A shows a structure of the filter unit 104a. Incidentally, a structure of the filter unit 104b is also common to the filter unit 104a. The intensity filter (ND filter), the polarizing filter, or the spatial filter is made to act on the transmitting scattered light components in the filter unit 104. The intensity filter is installed arbitrarily in order to balance amounts of the lights that enter a plurality of detectors. In the case where intensities of the scattered lights that arrive at the detectors 106a, 106b differ largely from each other and the detector with a large scattered light intensity saturates, the saturation can be avoided by acting the intensity filter on that optical path so as to dim the light. Moreover, by installing the polarizing filter, only a specific polarization component is transmitted, and therefore defect detection sensitivity can be improved. A polarizing filter is made up of a polarizing plate for transmitting a liner polarization component with a selected orientation, a wavelength plate, and a phase plate for giving an arbitrary phase difference or a phase plate whose phase difference is variable. The polarizing filter selectively shades or attenuates the light in an arbitrary state including an elliptical polarization. In the case where mutually different polarizations are transmitted, depending on a position, in an area through which light rays pass on a plane of the polarizing filter, a liquid crystal device, a spatial light modulating element, etc. are used. In the case where filtering using polarization is not performed, the polarizing filter retreats from on the optical path. In the exit pupil plane 104, a position at which a certain scattered light component arrived corresponds to an angle at which the scattered light is emitted from the inspection subject. Therefore, by installing a spatial filter that shades or transmits the scattered light component passing through a specific area in the exit pupil plane 104, the scattered light components of specific scattering angles are shaded or transmitted selectively. A light intensity distribution on the exit pupil plane 104 is observed by a pupil observation lens 110a and a pupil observation camera 111a. Based on information of the light intensity distribution monitored by the pupil observation camera 111a, setting of the spatial filter is done by a setup value that the operator inputted manually or by setup value automatically being set up. In order to set up a spatial filter while observing the exit pupil plane 104 in real time, a TV camera or the like is used as the pupil observation camera 111a.

FIGS. 5A and 5B show examples of shapes of shading parts and transmission parts of spatial filters each for improving the defect detection sensitivity. Incidentally, here, what is shown is an exit pupil in the case where the objective lens 102 is a Fourier transform lens, namely a spatial filter in the Fourier transform plane. FIGS. 5A and 5B show areas 121 corresponding to NA 1.0 in the Fourier transform plane, ranges that detection NA occupies in them, and shapes of the shading parts and the transmission parts by the spatial filters. With respect to a position 123 to which specularly reflected light of the illumination light by the substrate propagates, zeroth order diffracted light by the pattern formed on the inspection subject substrate comes in a sidewise direction (124) if the pattern is a lengthwise direction pattern, or comes in an oblique direction (125) if the pattern is an oblique direction pattern, or comes in a lengthwise direction (126) if the pattern is a sidewise direction pattern. Therefore, if the hatched area is shaded, the zeroth order diffracted light from a major pattern is shaded, and the defect detection sensitivity can be improved. In the case where the pattern has periodicities in the lengthwise direction and in the sidewise direction, higher order diffracted lights occur in a pitch corresponding to the repeating pitch of the pattern on the Fourier transform plane, in addition to the zeroth order diffracted light corresponding to the pattern of the lengthwise direction and the sidewise direction. Therefore, if a shading filter in the form of a grating for shading these, as shown in FIG. 5B, is provided, diffracted light from the pattern is shaded, and the defect detection sensitivity can be increased. In order to realize such a shading filter, an element of a mechanically driven shading plate or arrayed elements such that each cell can be selected as shading or allowing transmission (or reflecting) may be used. As examples of the latter, there are a DMD (digital mirror devices), an SLM (spatial light modulator), liquid crystal as examples of a two-dimensional array (FIG. 5C) a liquid crystal, a GLV (grating bulb), etc. as examples of a one-dimensional array (FIG. 5D).

Figure 6:
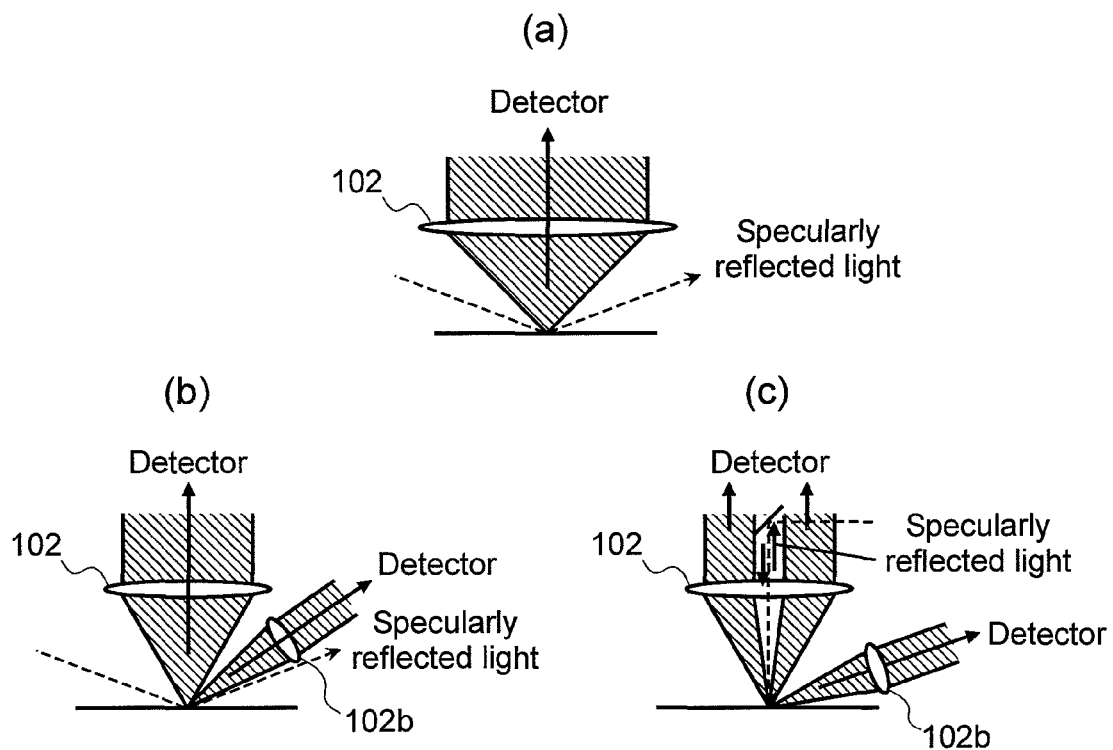

FIG. 6 shows a relation between a propagating direction of the illumination light by the illumination units and the detection unit. As shown in FIG. 6A, a configuration that specularly reflected light of the illumination light by the illumination units 101a, 101b does not enter the objective lens 102, i.e., a configuration of dark visual field detection is adopted. By this configuration, an image such that only a defect part, and a pattern part whose scattered light enters into the objective lens become bright and other parts than these parts becomes dark is obtained with the detectors 106a, 106b. For this reason, since high contrast is obtained in the defect part as compared with a case of the bright visual field detection that detects specularly reflected light components, it becomes possible to perform high-speed inspection with a large number of pixels while maintaining the defect detection sensitivity. As a concrete example, a case where detection of a defect whose size is 100 nm or less is performed is considered. In the bright visual field detection, it is necessary for a defect to be detected with a micro pixel of a size of about 0.2 µm while the image is being picked up; in the dark visual field detection, i.e., a case where the scattered light from the pattern part is suppressed on the inspection subject substrate, a defect can be detected with a micro pixel of a size of 0.5 µm to 2.0 µm can be detected. Provided that the number of pixels that can be processed per unit time is comparable with the former case, the latter can perform inspection with a high throughput 6.3 times to 100 times as much as the former. FIGS. 6B and 6C show modification examples of the configuration of dark visual field detection. FIG. 6B shows a configuration that performs the detection also with the objective lens 102b disposed slantingly in addition to the objective lens 102 above. The both are the dark visual field detection systems. This configuration can detect the scattered light components that emit in an elevation angle lower than that of the configuration only with the upper objective lens 102. FIG. 6C shows a configuration of performing coaxial vertical illumination such that light passes through the objective lens 102. Although the upper objective lens 102 allows also a specularly reflected light component to pass through, dark visual field detection becomes possible by shading this with the above-mentioned spatial filter. The illumination of a high elevation angle including the vertical illumination of FIG. 6C is effective in detecting defects, such as low-level-difference short circuit between the patterns of a high aspect ratio.

Figure 7:
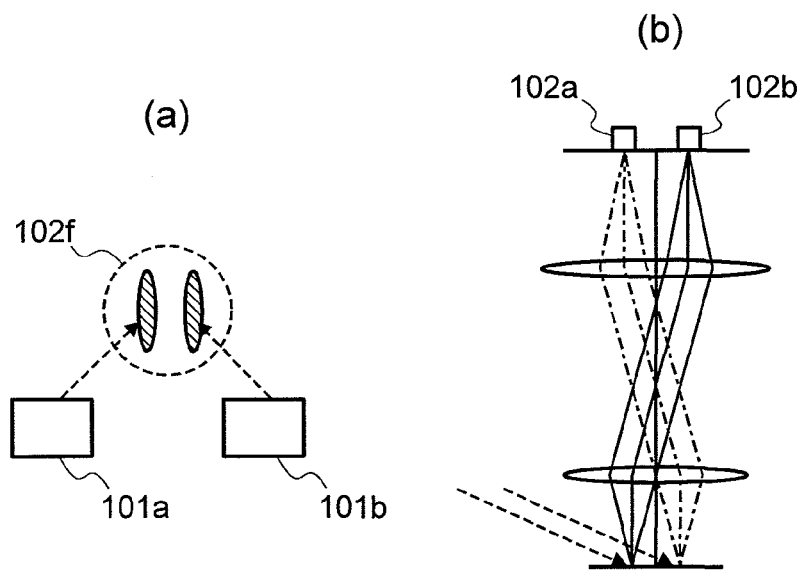

FIG. 7 shows modification examples of the illumination units 101a, 101b and the detection unit. As shown in FIG. 7A, each of the illumination units 101a, 101b illuminates the substrate so that the fields of illumination may not overlap mutually within the visual field 102f of the objective lens 102. As shown in FIG. 7B, imaging is done so that each field of the illumination may not overlap mutually on an image forming plane. The detectors 106a, 106b detect these, respectively. By setting illumination conditions (an elevation angle, an azimuthal angle, a polarization sate, and a wavelength) by the illumination units 101a, 101b so as to be mutually different in FIG. 3, the detectors 106a, 106b individually detect the plurality of scattered lights that are occurred correspondingly to a plurality of illumination conditions mutually different. By adopting a configuration that separates fields of illumination by a plurality of illumination units into spatially separated ones and detects the respective fields of illumination individually with the plurality of detectors, the plurality of scattered light distributions occurred correspondingly to a plurality of different illumination conditions mutually different are detected individually with the respective detectors.

Figure 8:
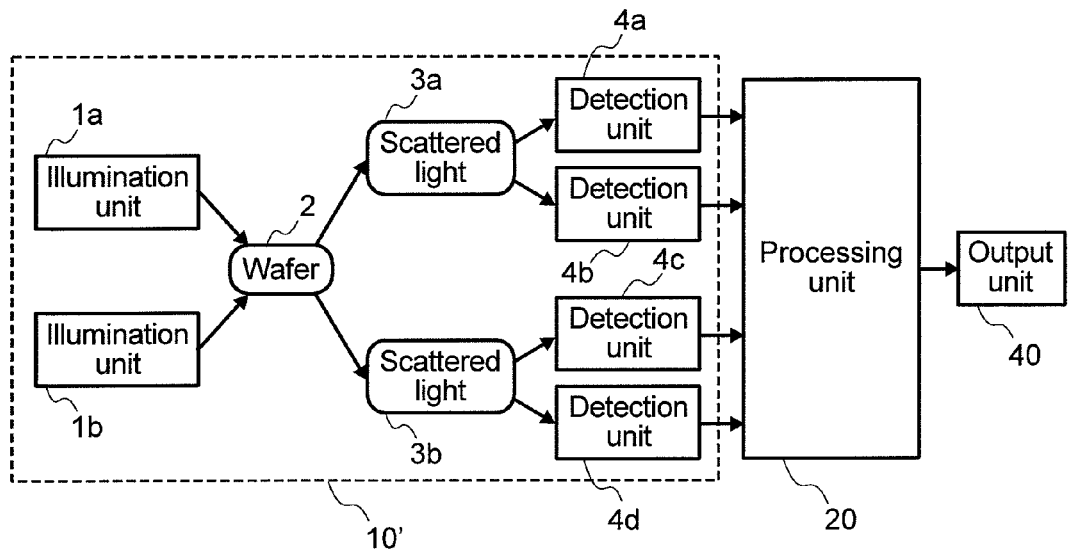
FIG. 8 is a block diagram showing a modification example of the defect inspection method related to the present invention.

FIG. 8 shows a modification example of the optical unit shown in FIG. 1. An optical unit 10' is constructed with the plurality of illumination units 1a, 1b, and a plurality of detection units 4a, 4b, 4c, and 4d. The illumination unit 1a and the illumination unit 1b irradiate mutually different illumination lights onto the inspection subject substrate 2. The illumination by the illumination unit 1a and the illumination unit 1b generates the scattered lights 3a, 3b, respectively, which is detected by the detection units 4a, 4b and the detection units 4c, 4d, respectively, as scattered light intensity signals. The detected scattered light intensity signals are inputted into the processing unit 20. The processing unit 20 outputs the defect information based on the plurality of scattered light intensity signals inputted therein. The output unit 40 outputs the defect information acquired by the processing unit 20.

Figure 9:
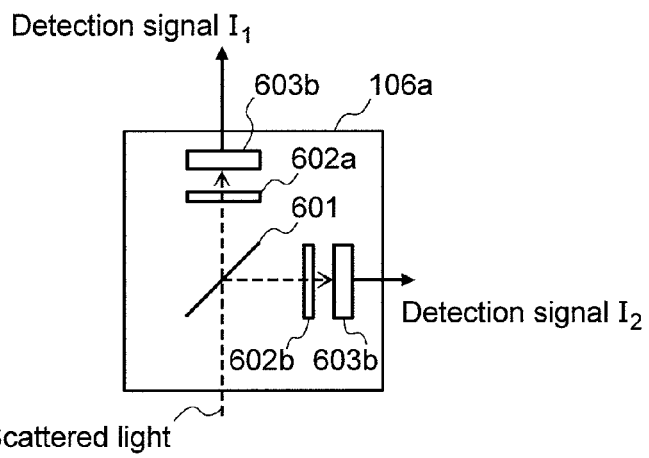
Figure 9:
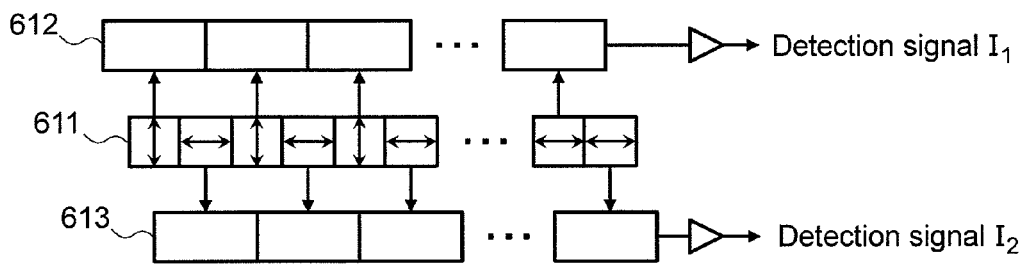

In the system configuration shown in FIG. 2, the configuration shown in FIG. 8 is realized using a detector capable of collectively detecting a plurality of optical components as the detectors 106a, 106b. FIG. 9 shows an example of the detector capable of collectively detecting a plurality of optical components. FIG. 9A shows a configuration that separates the scattered light according to the polarization condition by the polarizing beam splitter 601, and detects them with detectors 603a, 603b. Wavelength plates 602a, 602b for selecting an arbitrary alteration are installed as necessary. If the polarizing beam splitter 601 is substituted by an optical element having a wavelength selective function, such as a dichroic mirror, the detector will be of the same configuration as the 3-CCD sensor. Use of this enables the scattered light including a plurality of wavelengths to be separated on a wavelength-by-wavelength basis and detected individually. FIG. 9B shows an example of the detector for obtaining a plurality of detection signals that are derived from mutually different polarization components by configuring each photoreceiver pixel of the detector to detect a different polarization component. In the detector, mutually orthogonal polarizers are arranged one by one on linearly aligned photoreceiver pixels 611 so that each pixel may detect each of mutually different polarizations of two kinds. Such a photodetector is realized by aligning and cementing a polarizer array made by a method that is stated in U.S. Pat. No. 3,325,825 or the like to the pixels of linear sensor. If as the linear CCD sensor, one that signals of odd number pixels are outputted to a one-side horizontal transfer register 612 and signals of even number pixels are outputted to other-side horizontal transfer register 613 is used, outputs of the respective registers correspond to detection signals of the respective polarization components. The configuration of FIG. 9A has a feature that can realize high resolution as compared with a case of FIG. 9B. On the other hand, since the configuration of FIG. 9B can do with only one sensor, it features capability of being constructed cheaply.

Figure 10:
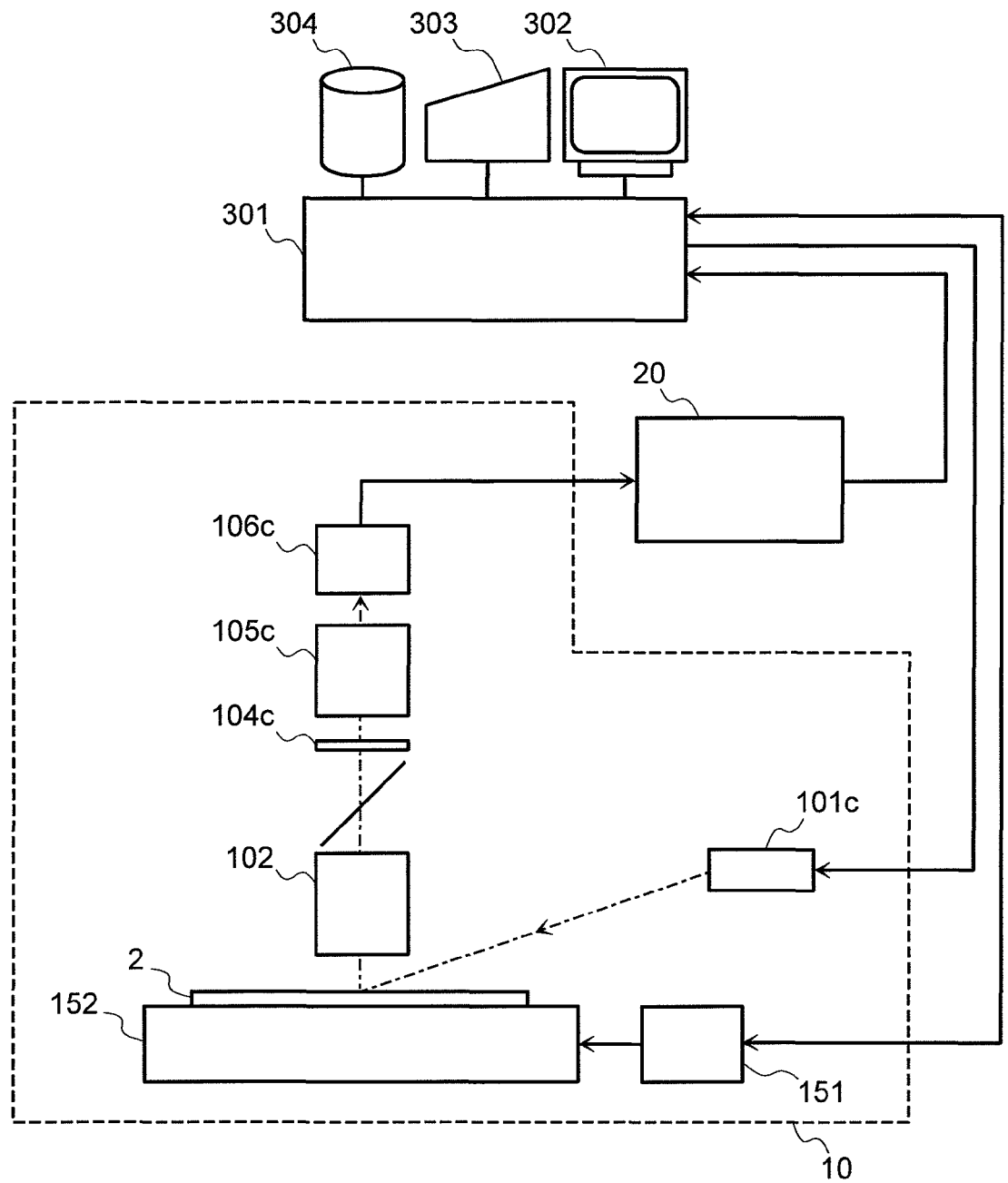
FIG. 10 is a configuration diagram showing a modification example of the defect inspection system related to the present invention.

FIG. 10 shows another system configuration example that realizes the configuration of FIG. 8. The optical unit 10 is constructed with an illumination unit 101c, the objective lens 102, a filter unit 104c, an imaging lens 105c, a detection unit 106c, the stage drive unit 151, and the X-Y-Z-θ stage 152. Other aspects of the configuration are common to the configuration example of the system shown in FIG. 2. This configuration enables the illumination conditions and the detection conditions to be changed temporally, which realizes the configuration of FIG. 8 using a single light source and a single detector.

Figure 11:
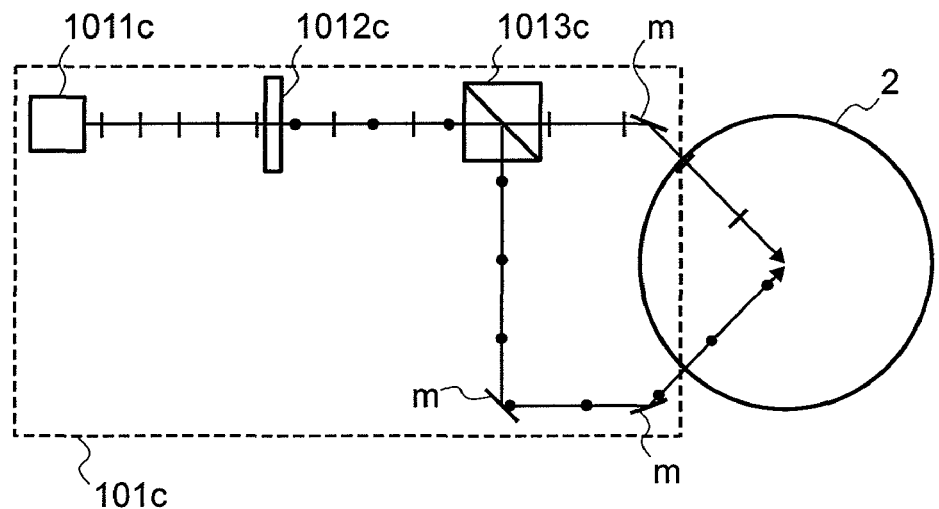
Figure 11:
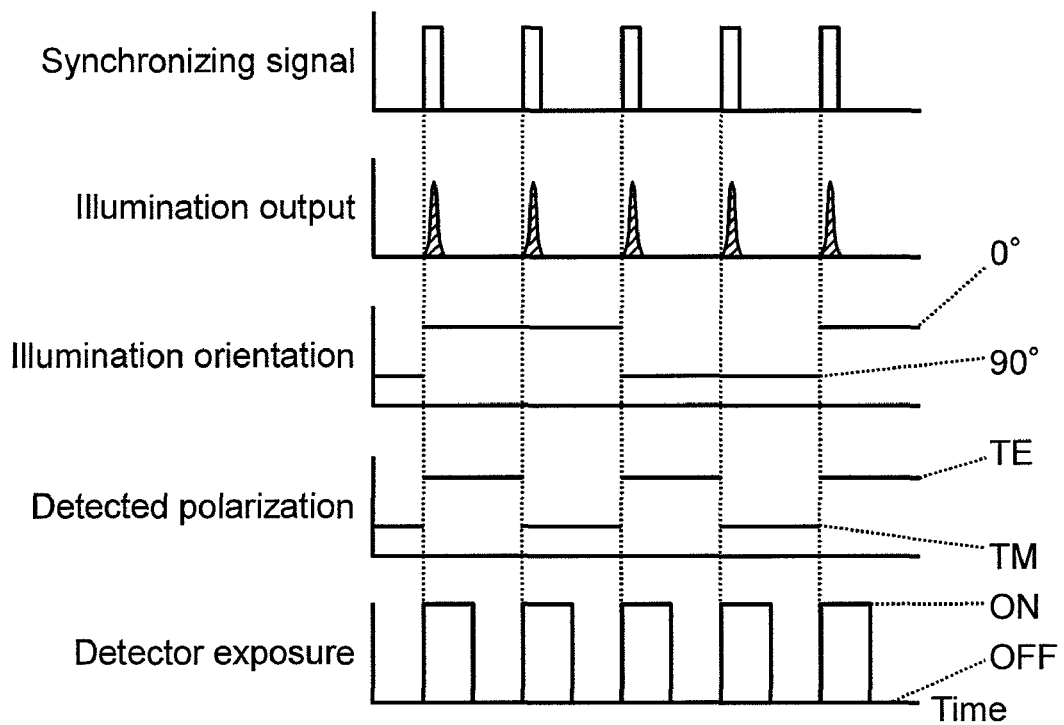

A concrete example of a method for changing the illumination conditions and the detection conditions temporally will be explained using FIG. 11. FIG. 11A shows a concrete example of a method for changing the illumination condition. As the light source 1011c, a pulsed laser or a flash lamp making periodical stroboscopic light emission is used. As a polarization modulation element 1012c, one that varies phase difference given to light periodically in synchronization with a period of stroboscopic light emission of the light source or its multiplication by an integer, for example, an electrooptical device, a magnetooptical device, an acoustooptic device, and a liquid crystal device, is used. By the polarization modulation element 1012c, the polarization state of the periodic pulsed light emitted from the light source changes temporally. By a polarizing beam splitter 1013c changing an optical path of the light according to its polarization state, an optical path through which the pulsed light passes is changed over temporally. By this switching, the identical place is illuminated while the polarization condition, the illumination orientation, the illumination incident angle, etc. are switched temporally. It is obvious that the equivalent function in terms of switching the illumination condition temporally can be realized also by switching the polarization state of the light using the polarization modulation element instead of the phase plates 1013, 1014 and separating the optical path according to the polarization state using the polarizing beam splitter instead of the mirrors M1, M2. If the spatial modulation element 104c is also used on the detection side to temporally switch a polarization distribution, a phase distribution, an intensity distribution of the light passing therethrough, an optical condition used for the detection can be changed temporally. As the spatial modulation element 104c, a liquid crystal device, an electrooptic device, a magnetooptic device, an acoustooptic device, a micro mirror device, a GLV (grating bulb), a shading plate driven mechanically, etc. are used.

FIG. 11B shows a pulsed illumination output, an illumination condition (illumination orientation, as an example), a detection condition (a polarization component to be detected, as an example), a temporal relation of ON/OFF of exposure of the detector with a horizontal axis representing time. Using a synchronizing signal outputted by the stage drive unit 151 as a reference, the illumination emits light in a pulsed mode, an illumination orientation and detected polarization are switched, and each of the scattered light distributions corresponding to the each pulsed light is detected individually by a single detector. Letting the illumination condition have as much as N (N=1, 2, . . . ) options and letting the detection condition have as much as M (M=1, 2, . . . ) options, the detection signals corresponding to combinations of the optical conditions up to N×M options can be acquired.

Figure 12:
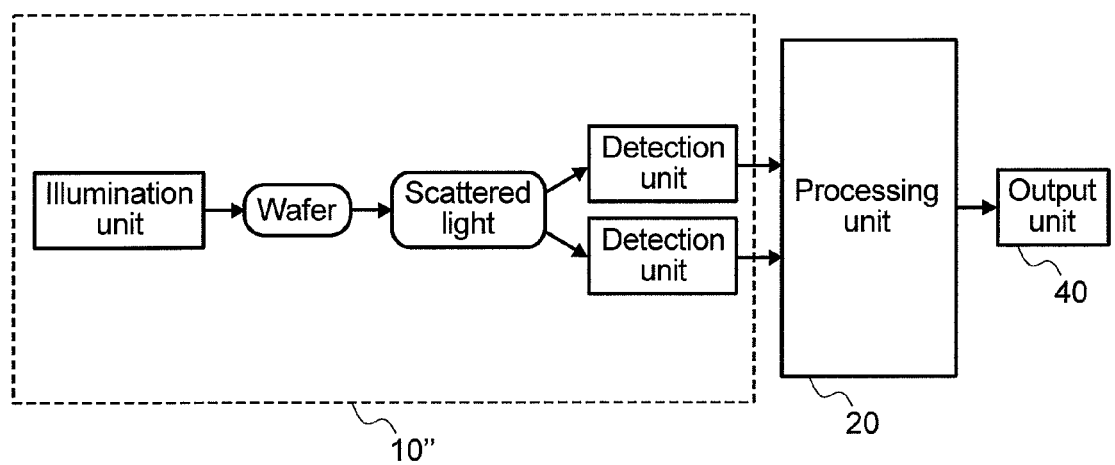
FIG. 12 is an explanatory diagram showing a modification example of an optical unit in the defect inspection system related to the present invention.
Figure 13:
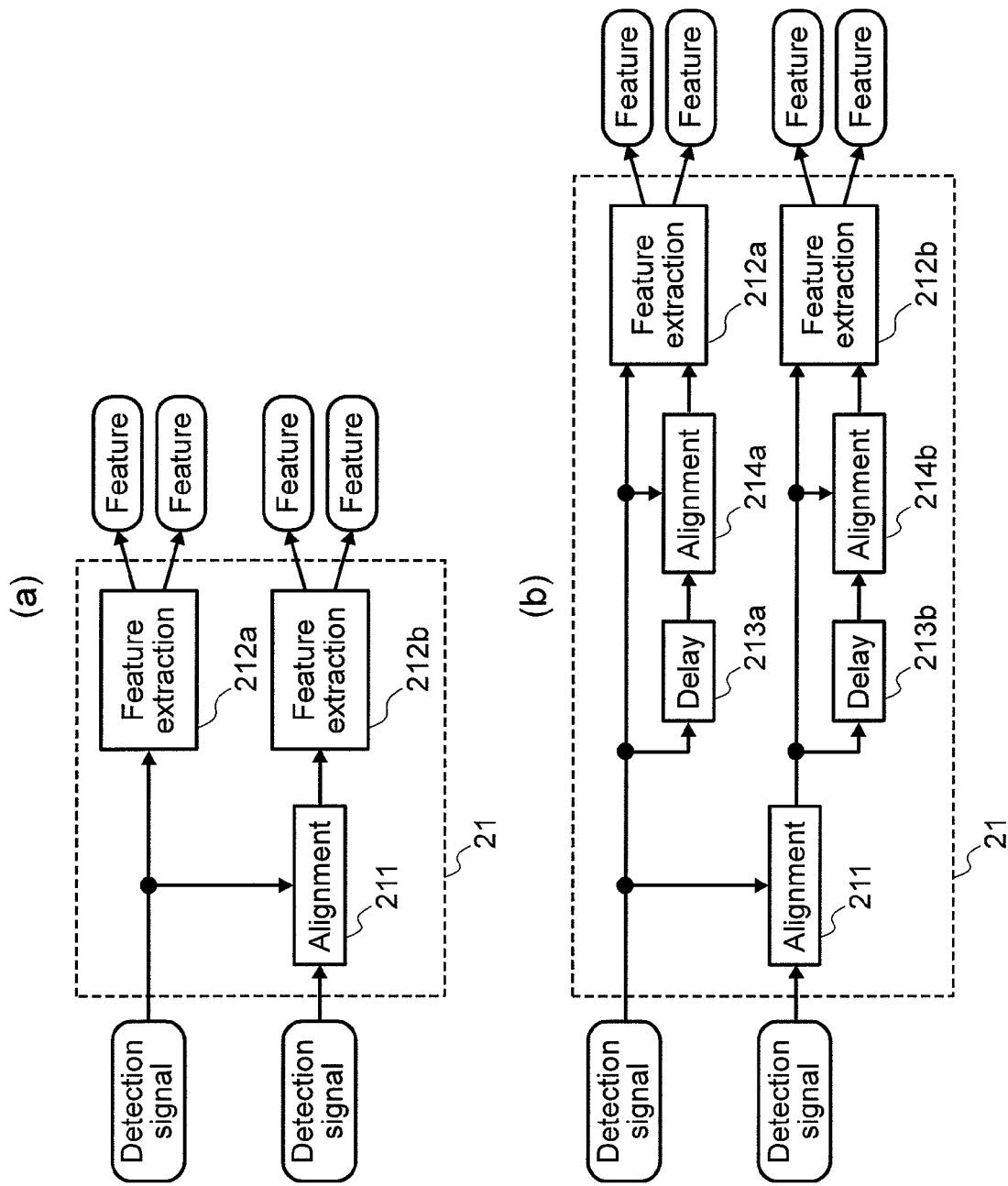
Figure 14:
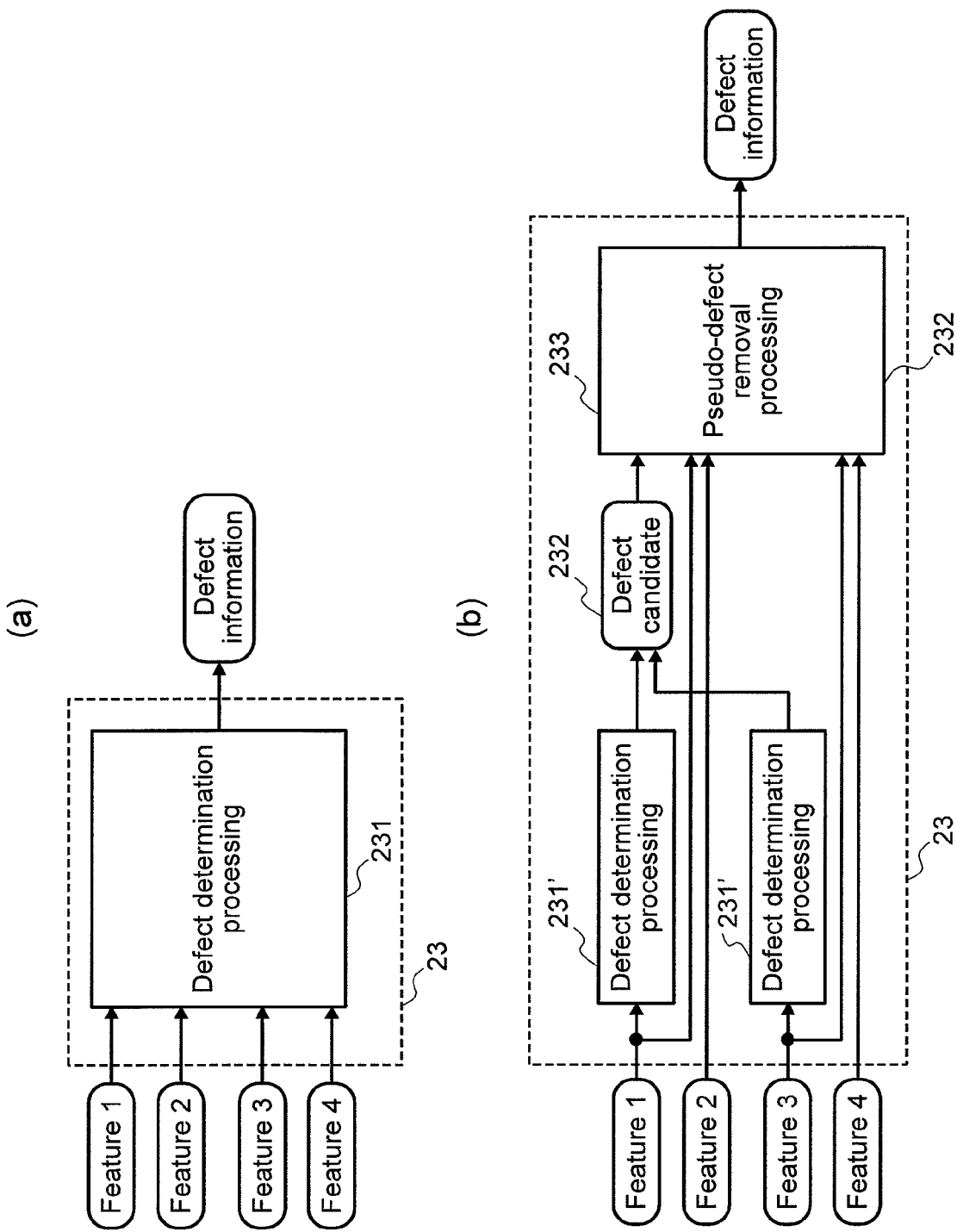

FIG. 12 shows another modification example of the configuration of the optical unit shown in FIG. 1. FIG. 12 shows a configuration where the scattered light occurred by the illumination given by the illumination unit is detected with a plurality of detection units. The illumination unit illuminates the inspection subject at the identical place under a plurality of illumination conditions or under a single illumination condition. The scattered light distribution occurred is unique. This is detected with the plurality of detection units to acquire a plurality of detection signals. This configuration does not have a configuration of switching the illumination condition by the illumination unit temporally (FIG. 11) or spatially (FIG. 7) or separating it according to wavelength (FIG. 3); accordingly, there is a merit that the system can be constructed cheaply.

FIG. 13A shows a configuration of the preprocessing unit 21. The detection signals acquired by a plurality of mutually different optical conditions are inputted into the preprocessing unit 21. Here, a case where the number of detection signals is two will be explained. The alignment unit 211 performs alignment by setting one detection signal as a reference and correcting other detection signals with respect to it. By comparing the detection signal serving as a reference and the other detection signal at each time interval or each position interval determined in advance, an amount of misalignment to be corrected is calculated. For the comparison method, a correlation value between the signals cut out in a predetermined range, an absolute value total of a difference between them, or the like is used. Much robust alignment becomes possible by using the following values as a signal of object to be compared: a value obtained by normalizing or binarizing an original detection signal intensity so that a discrepancies of the signal intensity due to a difference of the optical condition may be smoothed out; an edge position extracted by applying a filter to the detection signal; a code corresponding to signal intensity gradient direction, or the like. In the case where temporal misalignment between a plurality of detectors is small, if the detection signals of the identical place are obtained with the plurality of detectors in advance, the amount of misalignment is calculated, and the alignment is performed based thereon; real time alignment as the one described above becomes unnecessary.

The detection signals after the alignment are inputted into the respective feature extraction units 212a, 212b, respectively. The feature extraction units 212a, 212b process the detection signal, and output a value of feature of one image or a plurality of images for each coordinate (each set of coordinates) corresponding to one detection signal. What is necessary as the feature is just to exhibit a characteristic of the pixel. As one example of it, there are brightness (signal strength itself), contrast, a shading difference, a variance value of brightness of neighborhood pixels, a coefficient of correlation, increase/decrease of brightness to the neighborhood pixels, a second derivative value, etc.

FIG. 13B shows another configuration example of the preprocessing unit 21. Portions that are different from FIG. 13A will be explained. In the case where the same pattern is repeatedly formed on the inspection subject, the defect can be emphasized by accumulating a signal included in one unit of repetition and performing comparison processing of the same place that will appear in the next repetition with it. By accumulating the detection signal after alignment was done in a delay unit 213a and performing alignment between it and the same place that will appear at next repetition in an alignment unit 214a, signals of two places at which the same pattern should be formed are obtained. These signals are inputted into a feature calculation unit 212a. A signal accumulated in the delay unit 213a is called a reference signal. The feature extraction unit 212a processes the detection signal together with the reference signal at a position corresponding to it and outputs one or a plurality of image features per coordinate. As one example of the feature, there are brightness of the detection signal (signal strength itself), contrast, a shading difference, a variance value of brightness of neighborhood pixels, a coefficient of correlation, increase/decrease of brightness to the neighborhood pixels, a second derivative value, a difference absolute value between any of these values and its reference signal or a signed difference, etc.

FIG. 14A shows a configuration of the determination unit 23. The determination unit 23 is made up of a defect determination processing unit 231. The defect determination processing unit 231 performs defect determination processing based on the input of a plurality of features, and outputs the defect information. A method of defect determination based on the plurality of features performed in the defect determination processing unit 231 will be explained using FIG. 15.

FIG. 15A shows one example of the defect determination method in the case where the features are two (feature A, feature B). FIG. 15A is a scatter diagram in which the feature A and the feature B are plotted for each coordinate within a range of the processing subject area.

Figure 16:
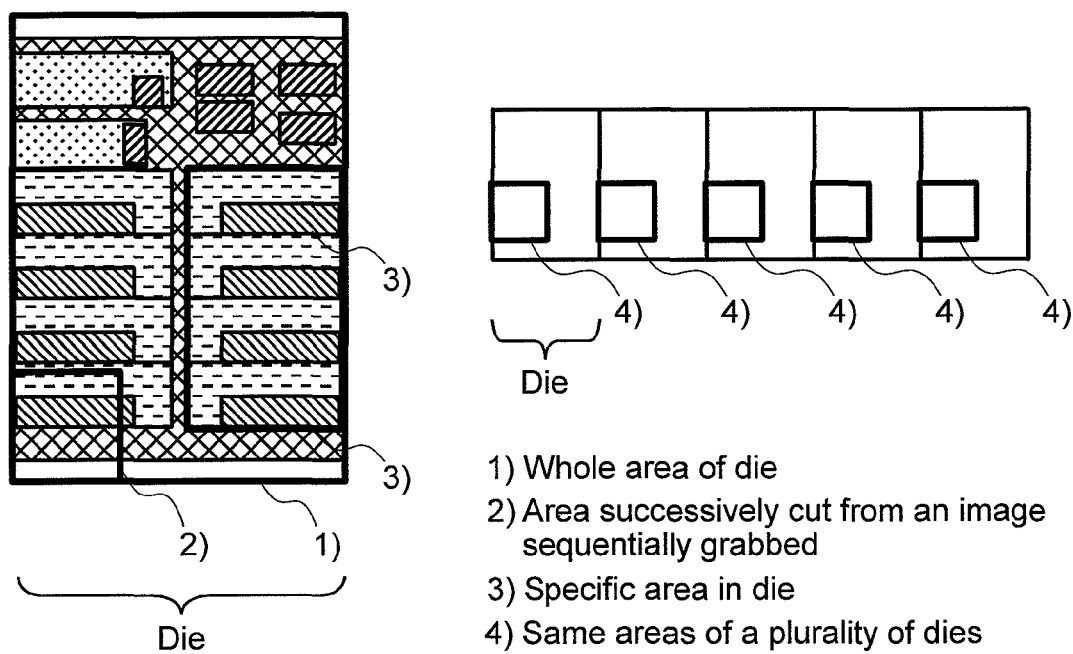
FIG. 16 is an explanatory diagram showing a processing subject area in the defect inspection method related to the present invention.

The processing subject area means an area that is assigned to be a unit of processing. FIG. 16 shows an example in which a semiconductor wafer or a reticle used for manufacturing the semiconductor wafer is considered as an inspection subject. If the defect determination processing unit 231 is equipped with much memory, it is possible to assign the whole area of die to be a processing unit. If the area of the processing unit is wide, the number of samples that are subjected to statistical treatment becomes large; therefore, reliability of defect determination will be improved. Alternatively, if an area in which successively grabbed image is sequentially cut out during when the inspection subject is scanned is designated as a processing unit, processing can be performed with comparatively less memory. Alternatively, if the area having a similar tendency in a die is cut out and designated as a processing unit, variation in feature in the normal part other than defect part becomes small and it is advantageous for improvement of the defect detection sensitivity. Alternatively, when corresponding areas in respective dies over a plurality of dies are cut out and each of them is designated as a processing unit, a variation in the feature in the normal part from which defects are excluded becomes small and it will be advantageous in improving the defect detection sensitivity.

It is expected that in the normal part other than the defect part, there are a plurality of portions each having the same physical feature, namely a shape, a material, etc. in the processing subject area. On the contrary, the defect part is comprised of singular points other than the normal part and there is a low probability that a portion having the similar physical feature exists in the processing subject area. Therefore, the defect determination is performed by determining that, if points on the scatter diagram corresponding to a plurality of positions gather closely, the positions are of the normal part, and by determining that if a point on the scatter diagram corresponding to a certain position is isolated away from gathering of a large number of other points, the position is of the defect part. FIG. 15B shows an example of a case where a larger number of features are used. By the same way of thinking as a case where two features are used, in the case of using N features, a scatter diagram will become that of an N-dimensional space, isolated points with a small number are determined as defects based on a magnitude of a length in the N-dimensional space.

FIG. 15C shows a scatter diagram of a large number of features compressed into two dimensions. The diagram corresponds to a plotting in which calculated values of a plurality of features are plotted onto the axes. By this method, a load of determination processing that determines a piece of data whose value is out as a defect can be mitigated. Calculation of the plurality of features includes: selecting a feature effective in defect determination from among a plurality of features; extracting effects of the plurality of features by weighting them by a linear combination of the plurality of features; etc. The selection of the feature to be used and weighting thereof are done so as to make it easy to determine the defect part by making points corresponding to the defect part on the scatter diagram away from a group of points corresponding to the normal part or by making them exhibit a characteristic distribution. A defect part has features in physical, optical, or statistical characteristics to the normal part, regarding its shape (irregularity, surrounding lengthwise structure and sidewise structure, periodicity, directivity), material, or dimensions. Such features of the defect part, namely differences between the defect part and the normal part are included as information in the scattered light distribution, which is a response to the illumination, a part of the information is detected by the detection unit as a detection signal, and further a part thereof is detected by the feature extraction unit as an image feature. In order to detect a defect with high sensitivity, the detection must have an illumination condition in which a feature of the defect part appears much in the scattered light distribution, or a detection condition where the feature of the defect part revealing in the scattered light distribution is grabbed without missing it, and further a feature extraction condition where the feature of the defect part appearing on the image is extracted better. Since according to a configuration of the illumination unit, the detection unit, and the feature extraction unit described above, a plurality of features corresponding to a combination of a plurality of mutually different illumination conditions, detection conditions, and feature extraction conditions can be detected simultaneously, there is a high possibility of grasping a characteristic of the defect part as compared to a configuration that the system is provided only with a single illumination condition, detection condition, or feature extraction condition. Further, by selecting a feature or a combination of features corresponding to the illumination condition, the detection condition, or the image processing condition that is effective from among a plurality of features detected simultaneously according to a method as shown in FIG. 15C, a characteristic of the defect part is represented as a distribution on the scatter diagram; therefore, determination of the defect based on it makes possible detecting the defect with high sensitivity and with a high capture ratio.

FIGS. 15C, 15D, and 15E show methods for determining the defect by means of a change among features under mutually different conditions. In comparison with the diagram of FIG. 15C, FIG. 15D shows a diagram of a combination of features or the features given weights that are different from FIG. 15C being plotted on the two axes. As shown in FIG. 15E, it is also possible to separate distributions of the defect part and of the normal part and thereby determine a defect by plotting the amount of change of the feature between FIG. 15C and FIG. 15D. This method is effective, for example, in the case where behavior of the scattered light distribution of the defect part or the normal part under a certain illumination condition A and behavior of the scattered light distribution under an illumination condition B that is different from A differs largely from each other. What is necessary to perform this method is just to select the feature corresponding to the illumination condition A regarding f and g in FIG. 15C, select the feature corresponding to the illumination condition B regarding f' and g' in FIG. 15D, and plot an amount of change on the scatter diagram between these diagrams as in FIG. 15E.

As an example of the illumination condition and the detection condition effective in actualizing the feature of the defect part, for example, in the case where there exists the defect part having a geometrical feature such that the defect is long in the X-direction and is short in the Y-direction in the normal part having a shape that is symmetrical in the X-direction and the Y-direction, the illumination condition of irradiating it with the illumination light from an orientation of the Y-direction vertical to the X-direction and the detection condition of detecting the scattered light emitting to the above are effective. In this case, in the scattered light distribution of the defect part, the scattered light intensity becomes intense in the above direction with respect to the scattered light distribution of the normal part, and a feature of the defect part is detected as a luminance signal more intense than the normal part. Moreover, in the case of a defect with directionality, it is also effective to select an illumination condition having a polarization component corresponding to the directionality or a detection condition of having a light detection state having a state of analyzer corresponding to the directionality. Like these examples, in the case where the illumination condition, the detection condition, or the feature extraction condition that is effective in making the defect manifest is evident, if the illumination condition, the detection condition, and the feature extraction condition to be used are narrowed in advance, or if a feature to be used for determination among the detected features is narrowed in advance as shown in FIG. 15C, the load of illumination, detection, feature extraction, or defect determination will become small, so that it will become possible to perform the inspection in a short time. On the other hand, even in a case where effective conditions are not clear, the defect can be detected with high sensitivity and with a high capture ratio by adopting the following method: A plurality of features detected simultaneously by the above-mentioned configuration are subjected to determination processing using various combinations or weightings; the defect determination results by these combinations/weightings are compared; and a determination processing method that outputs a suitable result is selected. A procedure required to select a determination method for outputting the above-mentioned suitable result and input/output of information will be described later using FIG. 17.

Another configuration example of the defect determination unit 23 will be explained using FIG. 14B. Parts (in FIG. 14B, a feature 1 and a feature 3) in a plurality of features outputted from the above-mentioned feature extraction unit are inputted into a defect determination processing unit 231'. The defect determination processing unit 231' performs defect determination by the same method as that in the defect determination processing in the above-mentioned defect determination processing unit 231. Note that the defect determination processing unit 231' performs defect determination with a criterion and a threshold lower than those of the defect determination processing unit 231, and outputs information of a group of a mixture of the defect part and the normal part, namely information of a group of defect candidates (corresponding coordinates) 232. A pseudo-defect removal processing unit 233 in a later stage is inputted with coordinates 232 of the group of defect candidates and a plurality of features outputted from the above-mentioned feature extraction unit, and performs the pseudo-defect determination processing (FIG. 15F). Pseudo-defect determination processing targets only the group of defect candidates, performs the same processing as the above-mentioned defect determination processing unit 231 based on a feature of each defect candidate, and performs a determination of the defect part, and here in addition to it, removal of the normal part (pseudo-defect) included in the defect candidates. In the configuration of FIG. 14A described above, a processing load becomes large because defect determination based on a large number of features regarding a large number of positions on the inspection subject is performed, whereas in the configuration of FIG. 14B, defect candidate positions are narrowed based on a small number of features regarding a large number of positions on the inspection subject in the previous-stage defect determination processing unit 231', and the defect determination based on a large number of features is performed only regarding a small number of defect candidate positions after the narrowing, whereby a net processing load is reduced.

Figure 15:
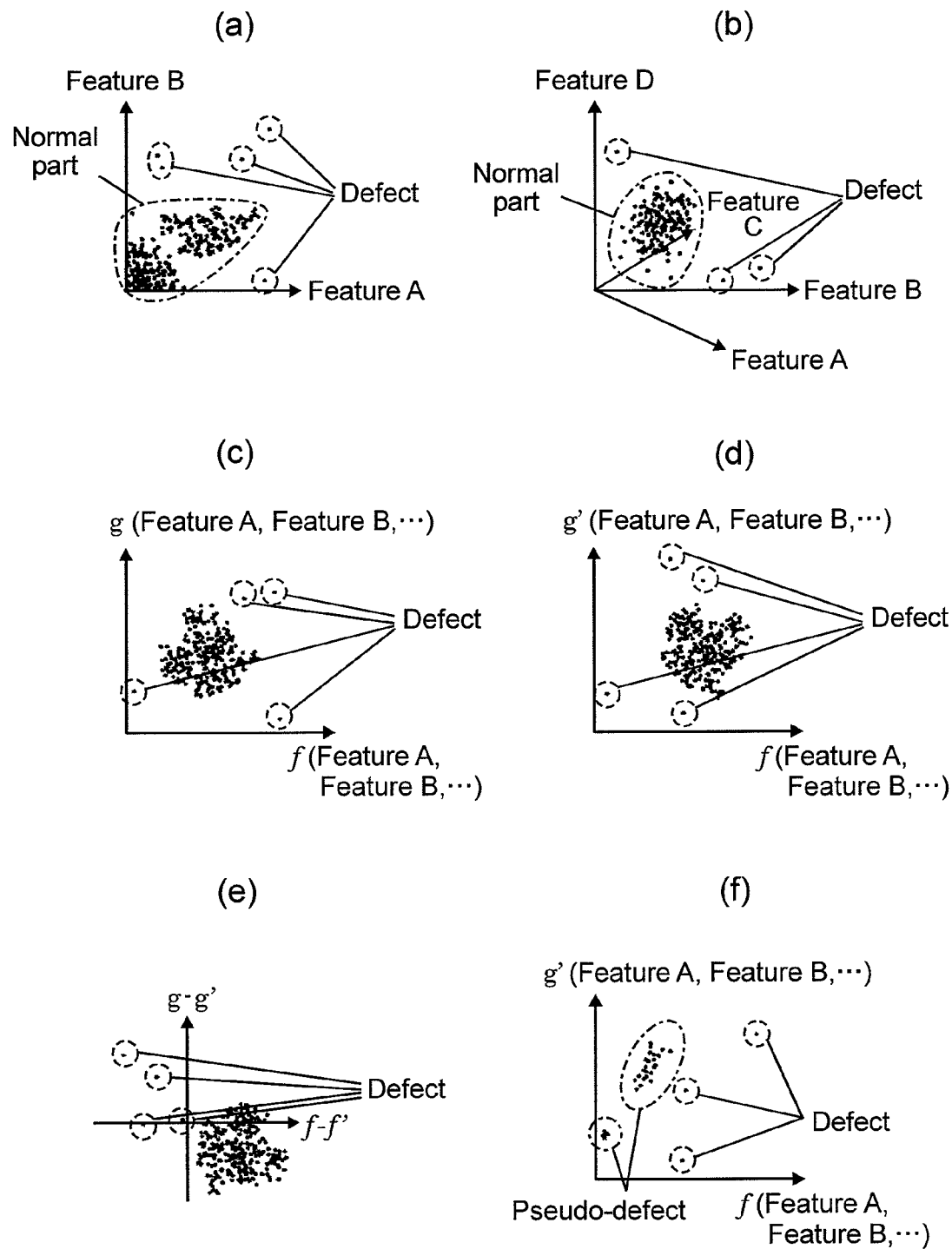
Figure 17:
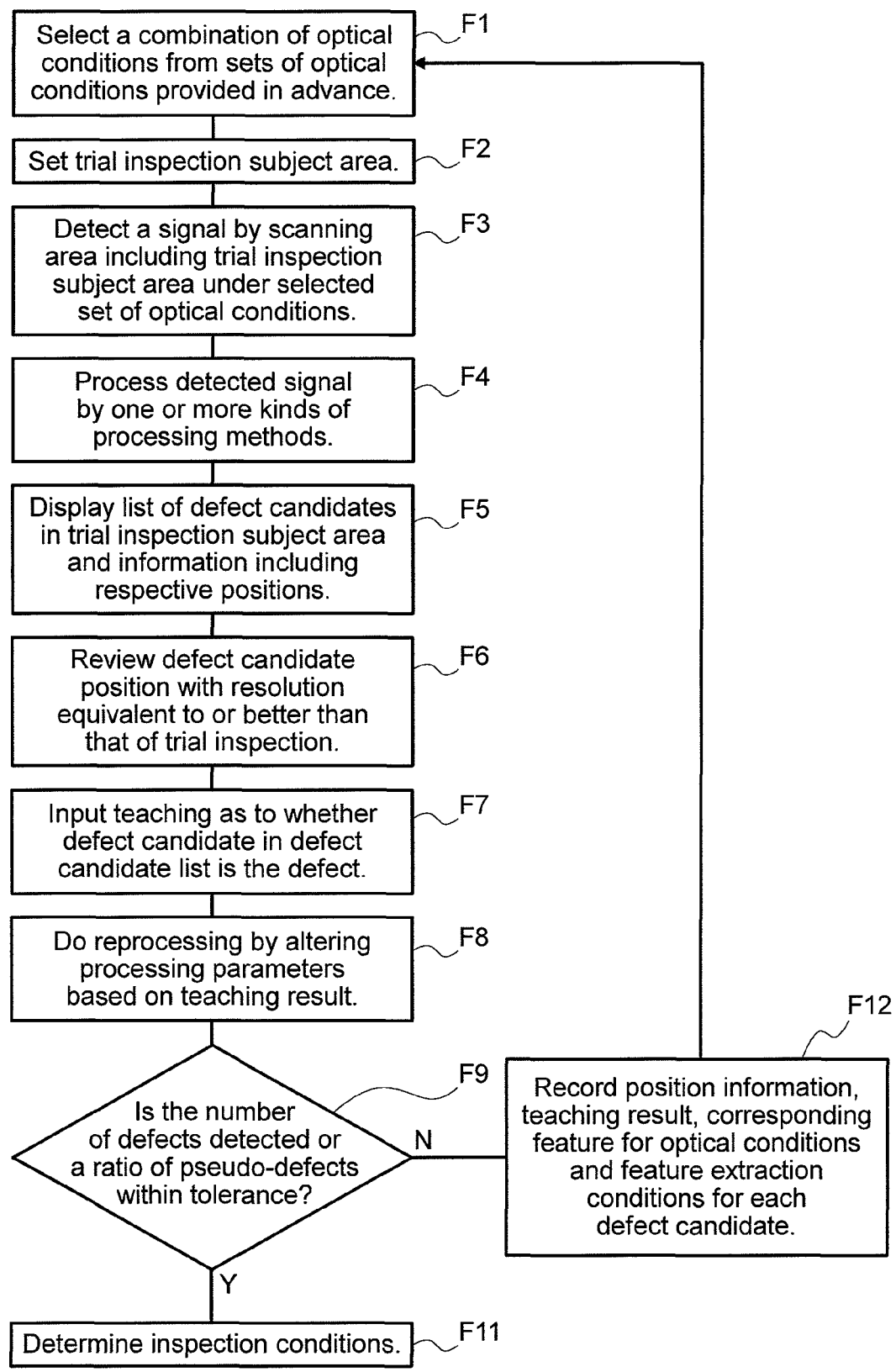
FIG. 17 is a flowchart of inspection condition setup in the defect inspection method related to the present invention.

FIG. 17 shows a flowchart of setting inspection conditions (an optical condition, a feature extraction condition, and a defect determination processing method) Based on the user's input etc., a combination (set) of optical conditions is selected from among combinations of a plurality of optical conditions (an illumination condition and a detection condition) that are provided in advance (F1). Next, based on the user's input etc., an area to be subjected to trial inspection that is conducted in order to determine the optical condition, the feature extraction condition, and the defect determination processing method is set up (F2). An area including the trial inspection subject area is scanned, and a detection signal is detected under the selected optical condition set (F3). The detection signal is processed by one or more kinds of processing methods as shown in FIG. 15 (F4). A list of defect candidates in the trial inspection subject area and information on the defect candidates including respective positions and features are displayed (F5). The defect candidate positions included in the defect candidate list are reviewed by a review microscope provided in the system with resolution comparable to or better than that of the trial inspection, namely a static image at the position is acquired. In addition that a static image at the defect candidate position is obtained using the review microscope provided in the system, it may be all right that an image obtained at the time of scanning of the trial inspection is stored in the storage unit and is used, and that an image obtained by a defect review SEM, a critical dimension SEM, a desk-top SEM, an AFM, or the like based on the defect candidate position outputted by the system is used (F6). For each defect candidate, the image obtained by the review is displayed in the display unit, and teaching as to whether it is an actual defect by decision based on the image is inputted (F7). Based on the teaching result, parameters of defect determination processing are altered and re-processing is performed (F8). The results of re-processing rework are outputted in the display unit, and it is determined whether the following parameters are within a tolerance in terms of manufacture process control (F9): the number of detected defects, a defect capture ratio (a ratio of the number of defects each detected as an actual defect in the re-processing to the number of defect candidates each taught as a defect), a ratio of pseudo-defect (a ratio of the number of defect candidates each taught not as a defect among the number of defects each detected as an actual defect in the re-processing), etc. If it is within the tolerance, the inspection condition will be determined there (F11). If it is out of the tolerance, the condition and the result of the trial inspection (for each defect candidate, the feature corresponding to each position information, a teaching result, an optical condition and a feature extraction condition) are stored in the storage unit, the flow returns to F1, another optical condition set is selected by comparing the condition of the past trial inspection and the result, and the trail inspection is conducted again.

In the foregoing, the invention made by the present inventors was explained concretely based on the embodiments. However, it is natural that the present invention is not limited to the above-mentioned embodiments, or rather can be modified in various manners without departing the gist and scope of the present invention.

What is claimed is:
1. A defect inspection method, comprising:
emitting periodic pulsed illuminating light from a light source;
polarizing the periodic pulsed illuminating light into a plurality of polarization states;
splitting the periodic pulsed illuminating light into beams, wherein a beam differs from another beam in polarization state and illumination orientation;
changing illumination orientations of beams, while keeping their polarization states unchanged;
illuminating the beams that differ from one another, both before and after changing their illumination orientation, onto a predetermined area of an inspection subject substrate, such that the beams generate scattered light components;
detecting images of the predetermined area that differ temporally from one another, and some of which differ in polarization state and/or illumination orientation, wherein the image detection is based on scattered light components guided to a detector in a predetermined range of an azimuthal angle and in a predetermined range of an elevation angle, and wherein each image is affected by the polarization state and illumination orientation of the beam that generated the scattered light components;

extracting values of features from the images of the predetermined area; and determining a defect by finding a value that deviates from a relationship between values of the features of the images.

2. The defect inspection method according to claim 1, wherein a lamp light source is used to emit light.

3. The defect inspection method according to claim 1, wherein scattered light components are shaded or attenuated by a spatial filter before being detected by the detector used for obtaining the images.

4. A defect inspection method for inspecting a defect on an inspection subject on a substrate, comprising:

generating periodic pulsed illuminating light from a light source, under a plurality of optical conditions, including different polarization states and illumination orientations;

illuminating the periodic pulsed illuminating light onto a predetermined areas of an inspection subject substrate, thereby generating scattered light;

obtaining images that differ temporally, and some of which differ in polarization state and/or illumination orientation, of the predetermined area of the inspection object, by guiding onto a detector the scattered light resulting from illuminating the periodic pulsed illuminating light onto the inspection subject substrate;

extracting, from the images of the predetermined area, values of features of the predetermined area; and determining a defect in the predetermined area of the inspection object, based on statistical analysis of one or more correlations between values of features, wherein a value that deviates from a predetermined criterion is determined to be a defect.

5. The defect inspection method according to claim 4, wherein the periodic pulsed illumination light has mutually different wavelengths illuminated under the set of optical conditions.

6. The defect inspection method according to claim 4, wherein scattered lights are shaded or attenuated, and then individually detected for obtaining the images.

7. The defect inspection method of claim 4,
wherein a feature space is created by using an axis for each feature, in which values of two or more features are plotted for the predetermined area of an inspection subject substrate, and wherein outliers are identified as defects.

8. The defect inspection method of claim 4,
wherein a plurality of features are compressed into a base two dimensional feature space, by respectively multiplying values of the plurality of features with a base set of weighting parameters, thereby creating a base plurality of weighted values of features, and thereafter summing subsets of weighted values of features to create linear relationships between subsets of features.

9. The defect inspection method of claim 8,
wherein a plurality of features are compressed into an additional two dimensional feature space, by respectively multiplying values of the plurality of features with an additional set of weighting parameters, thereby creating an additional plurality of weighted values of features, and thereafter summing subsets of the additional weighted values of features to create additional linear relationships between subsets of features.

10. The defect inspection method of claim 9,
wherein a difference is calculated between the base two dimensional feature space and the additional two dimensional feature space, and a difference is calculated between the respective plurality of weighted values of features thereof, and outliers resulting from the difference calculation are determined to be defects.

11. The defect inspection method of claim 4,
wherein a second criterion, with a threshold lower than a threshold used with the predetermined criterion, is used to produce defect candidates with values of features not within the threshold of the second criterion;
wherein the defect candidates include both defective features and pseudo-defective features that are normal; and
wherein pseudo-defect determination processing is used to remove pseudo-defective features from the group of defect candidates.

12. A defect inspection method, comprising:
emitting periodic pulsed illuminating light from a light source, the periodic pulsed illuminating light being in the form of a beam having a plurality of different wavelengths;
redirecting an optical path of the beam, by using mirrors;
illuminating the periodic pulsed illuminating light onto a predetermined area of an inspection subject substrate, thereby generating scattered light components;
detecting images that differ temporally, and some of which differ in wavelength, by guiding to a detector scattered light components propagating in a predetermined range of an azimuthal angle and in a predetermined range of an elevation angle;
extracting values of features from the detected images of the predetermined area; and
determining a defect in the predetermined area of the inspection object, based on statistical analysis of one or more correlations between values of features, wherein a value that deviates from a predetermined criterion is determined to be a defect.

13. The defect inspection method according to claim 12, wherein a cylindrical lens is used to form a field of illumination on the inspection subject substrate, in the form of a line, a rectangle, or circle.

14. The defect inspection method according to claim 12, wherein the periodic pulsed illumination light is focused by a lens onto an area of a field of illumination on the inspection subject.

15. The defect inspection method according to claim 14, wherein a cylindrical lens is installed to form a field of illumination on the inspection subject substrate in the form of a line or in the form of a rectangular or circle.

16. The defect inspection method of claim 12, further comprising:
polarizing the periodic pulsed illuminating light into a plurality of polarization states.

* * * * *